United States Patent
Imai et al.

(10) Patent No.: US 6,169,186 B1
(45) Date of Patent: Jan. 2, 2001

(54) BISMALEIMIDES COMPRISING MESOGENIC GROUPS

(75) Inventors: Masaru Imai, Gunma (JP); Rainer B. Frings; Gerwald F. Grahe, both of Berlin (DE); Joji Kawamura, Chiba; Naoki Obi, Tokyo, both of (JP)

(73) Assignee: Dainippon Ink and Chemicals, Inc., Tokyo (JP)

( * ) Notice: Under 35 U.S.C. 154(b), the term of this patent shall be extended for 0 days.

(21) Appl. No.: 09/472,013

(22) Filed: Dec. 27, 1999

(30) Foreign Application Priority Data

Dec. 29, 1998 (EP) .................................. 98124805

(51) Int. Cl.⁷ ......................... C07D 403/12; C09K 19/08
(52) U.S. Cl. ........................................... 548/521; 544/372
(58) Field of Search ........................... 548/521; 544/372; 252/299.61

(56) References Cited

U.S. PATENT DOCUMENTS

| | | | |
|---|---|---|---|
| 5,114,612 | 5/1992 | Benicewicz et al. | 252/299 |
| 5,159,030 | 10/1992 | Hefner, Jr. | 525/502 |
| 5,314,513 | 5/1994 | Miller et al. | 51/295 |

FOREIGN PATENT DOCUMENTS

| | | |
|---|---|---|
| 318 162 | 5/1989 | (EP) . |
| 503 097 | 9/1992 | (EP) . |
| 878 482 | 11/1998 | (EP) . |
| 89/11867 | 2/1994 | (WO) . |

OTHER PUBLICATIONS

RAO T.V.S. & Lawrence D.S.: "Self–assembly of a threaded molecular loop" Journal of the American Chemical Society, vol. 112, No. 9, Apr. 25, 1990, pp. 3614–3615, XP002107363 *p. 3615, col. 2, line 5—line 20*.

Kitzerow H.–S.: "Polymer–dispersed liquid crystals. From the nematic curvilinear aligned phase to ferroelectric films" Liquid Crystals, vol. 16, No. 1, Jan. 1, 1994, pp. 1–31, XP000418459.

Chielline E. et al.: "Chiral liquid crystalline polymers: Recent issues and perspectives" Die Makromelekulare Chemie, Macromolecular Symposia, vol. 69, May 1, 1993, pp. 51–64, XP000381629.

Colomer F.R. et al.: "Side–chain liquid crystalline poly(N–maleimides). 5. Dielectric relaxation behavior of liquid crystalline side–chain and amorphous poly(N–maleimides). A comparative structural study" Macromolecules, vol. 26, No. 1, Jan. 4, 1993, pp. 155–166, XP000330544.

*Primary Examiner*—Fiona T. Powers
(74) *Attorney, Agent, or Firm*—Armstrong, Westerman, Hattori, McLeland & Naughton

(57) ABSTRACT

The invention relates to bismaleimides comprising mesogenic groups which consist, corresponding to (I), of two reactive terminal maleimide groups which are linked via linear or singly alkyl-substituted alkylene chains A, which are linked to an aromatic mesogen M via ester, amide or ether groups,

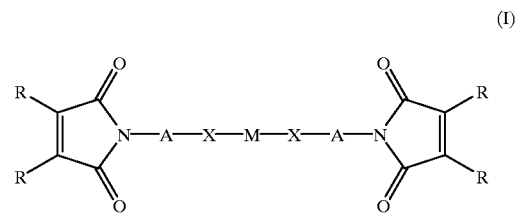

(I)

wherein A, X, M and R are as defined in the specification. The invention, moreover, relates to oligomeric liquid crystalline bismaleimides of general formula (II)

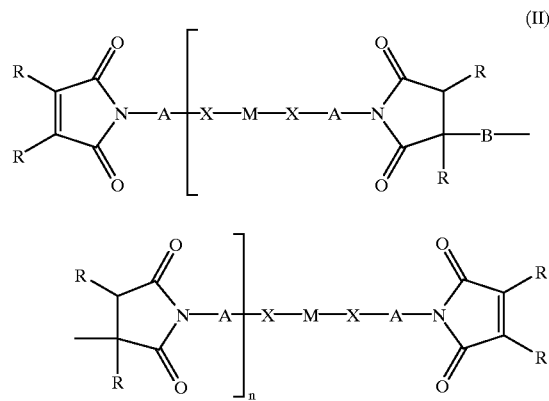

(II)

wherein A, X, M and R are as defined above, n represents and integer from 1 to 100 and B represents piperazinyl or a divalent radical which is derived from a primary or secondary para-substituted cyclic diamine, wherein B is bonded via the amino groups of the diamine. The invention also relates to methods of producing said bismaleimides.

13 Claims, No Drawings

BISMALEIMIDES COMPRISING MESOGENIC GROUPS

This invention relates to new bismaleimides comprising mesogenic groups and to methods of producing them.

Polymeric networks with liquid crystalline properties are materials which are potentially of interest, since they are capable of preferentially exhibiting outstanding mechanical and optical properties in their oriented state. Amongst the optical properties of networks of this type, the change in birefringence and the direction of polarisation in electric, mechanical and magnetic fields, which are utilised for the storage and display of information, e.g. in polymer network LCDs, should be emphasised in particular. In thermally crosslinked materials a reinforcement by liquid crystalline phases results in an increase in the modulus of elasticity, in the bending and fracture strength, and in hardness.

Mesogenic compounds are suitable for the synthesis of liquid crystalline crosslinking agents. Mesogenic compounds such as these are mainly aromatic compounds comprising at least two benzene rings, which are linked para to each other by suitable groups, such as ester-(—COO—), amide (—CONH—) or azomethine (—CH=N—) groups for example, wherein the terminal aromatic rings are each substituted in the para position in relation to these linking groups by an —OH, —COOH or —NH$_2$ group.

In order to attain liquid crystalline properties, the mesogens generally also have to be linked to suitable spacer chains via the aforementioned reactive —OH, —COOH or —NH$_2$ groups. The liquid crystals which are thus formed exhibit what are predominantly nematic textures under the polarising microscope.

If the spacer chains of the mesogens which were schematically described above have functions at their ends which are capable of crosslinking, such as acrylate, vinyl ether or glycidyl ether—groups for example, liquid crystalline compounds of this type are self-crosslinking or are capable of crosslinking with other reactive compounds by copolymerization. Their solubility in solvents, compatibility with the oligomeric and polymeric reactants and the liquid crystalline temperature ranges depend on the length of the linear aliphatic spacers, which may have a length corresponding to 1 to 30, preferably 3 to 20 CH$_2$ groups. Due to the spacer chains, the mesogens which form the liquid crystalline phase are isolated from the crosslinking sites, which is advantageous for the formation and for the capacity of orientation of the mesogenic phase. Examples thereof include liquid crystalline diglycidyl ethers, such as those described by D. J. Broer et al. in Macromolecules, 26, 1244–47 (1993) and by B. Koscielny et al. in Polymer Bulletin, Vol. 32 (5–6), 529–36 (1994), as well as diacrylate and divinyl ethers, such as those described by R. A. M. Hikmet et al. in Macromolecules 28, 3313–27 (1995) and in Polymer, 34, 1736–40 (1993).

As essential characteristic property for the existence of liquid crystallinity is the length/diameter ratio of the individual molecule, which should reach or exceed a value of 5. When the above mesogens are used, the resulting networks also predominantly exhibit nematic behaviour.

The industrial use of liquid crystalline crosslinking agents for the synthesis of mesogenic networks has hitherto foundered because of the costly synthesis of compounds of this type, which cannot be employed in an economically and technically feasible manner on an industrial scale. Multistage syntheses using protective groups are necessary in many cases, as described, for example, by M. Ando and T. Uryu in J. Polymer Science, Part A, 28, 2575–84 (1990) for liquid crystalline diacrylates. This publication describes the general procedure which was known hitherto for the synthesis of crosslinking agents of this type, which consists of reacting previously prepared bifunction mesogens, which comprise aromatically bonded para-substituted reactive —OH, —COOH or —NH$_2$ groups or halogen atoms, mainly fluorine, bromine or iodine, in a Williamson ether synthesis with an excess of an α,ω-dihalo- or dihydroxyalkane, whereby the polyalkylene chains which are necessary as spacers are introduced. If α,ω-dihydroxyalkanes are used, an OH function generally has to be protected by a suitable reversible protective group before di-substitution. A reaction with compounds which contain a group which is capable of polymerization is not effected until the end, optionally after the removal of the protective groups.

The groups which are employed as crosslinking groups are frequently those which are only capable of reacting with themselves or with a limited selection of other groups. Examples include the aforementioned acrylate, methacrylate and vinyl ether functions, which crosslink in addition polymerization reactions with compounds which contain groups of the same type or similar groups, or such as glycidyl ethers, which react with few other compounds, such as dicarboxylic acids, anhydrides or diamines. Moreover, liquid crystalline crosslinking agents which comprise said active crosslinking groups always require initiators or catalysts in order to initiate the reaction.

The object of the present invention was to identify liquid crystalline crosslinking agents which can be produced in as simple a manner as possible, and which can be produced in a simpler, less costly manner, even on an industrial scale, than the mesogenic crosslinking agents known hitherto, which could only be obtained in laboratory syntheses. At the same time, the object was to identify a method which was equally suitable for the production of as many different products as possible which differ only as regards their mesogen and by the length of their spacer group, so as to produce suitable products for as many areas of application as possible. In order to achieve this object, the number of reaction steps required for the formation of liquid crystalline crosslinking agents have had to be significantly reduced and the few steps which were required must proceed with a high yield and be only slightly dependent, or not dependent at all, on the structure of the reactants.

The present invention relates to bismaleimides comprising mesogenic groups, which consist, corresponding to formula (I) given below, of two reactive terminal maleimide groups which are linked via linear or singly alkyl-substituted alkylene chains A, which are linked to an aromatic mesogen M via ester, amide or ether groups,

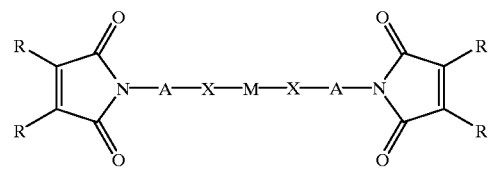

(I)

wherein A independently represents an alkylene chain comprising 3 to 20 CH$_2$ groups, wherein one C atom of each alkylene chain A can be chiral due to alkyl substitution, X independently represents —C(O)O—, —C(O)NH— or —O—, and M represents a mesogen consisting of at least two rings including an aromatic or a heterocyclic ring, which are linked para to each other by single bond, —CH$_2$—

$CH_2$—, —CH=CH—, —C≡C—, ester (—COO—), amide (—CONH—), methylstilbene (—C($CH_3$)=CH—), azomethine (—CH=N—), azine (—CH=N—N=CH—), azo (—N=N—) or azoxy (—N(O)=N—) groups, and which can be mono- or di-substituted by alkyl groups, wherein the terminal aromatic rings are each substituted in the para position to these linking groups by an O or NH group of X, and R independently represents an H atom, an alkyl group comprising 1 to 8 C atoms, a phenyl ring or a halogen atom.

Unless otherwise stated, the term "alkyl" denotes a hydrocarbon group comprising 1 to 5 carbon atoms, such as methyl, ethyl, propyl, butyl and pentyl, including the isomers thereof. Methyl is preferred.

The bismaleimides of formula (I) according to the invention can be produced from maleimidoalkylcarboxylic acids, the single-stage synthesis of which is described in EP-A-0 847 991, by linking the acid chlorides thereof, which can be obtained in a simple manner and in good yield, with difunctional aromatic mesogens.

Therefore, the present invention further relates to a method of producing bismaleimides comprising mesogenic groups of general formula (I) as defined above, in which X represents —C(O)— or —C(O)NH—, wherein maleimidoalkylcarboxylic acids of general formula

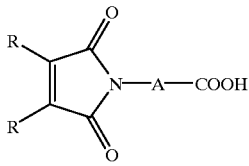

wherein R and A are as defined above, are converted into the corresponding acid chloride, 2 equivalents of the acid chloride are reacted with a compound of formula

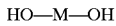

or

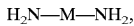

wherein M is defined above, in a suitable solvent, optionally in the presence of a catalyst and/or an acid acceptor, and at a temperature of 0 to 70° C., and the bismaleimide is isolated.

The essential advantage of the maleimidoalkylcarboxylic acids which are described in EP-A-0 847 991 and which are used for the production of bismaleimides of formula (I) according to the present invention is that the polymerisable function comprising a spacer group, which consists of 1 to 20, preferably of 3 to 12 $CH_2$ groups, one of which can be chiral due to substitution by alkyl, already exists in them, and is linked to a reactive, terminal —COOH group.

The bismaleimides comprising mesogenic groups according to the invention which are produced in this manner may exhibit liquid crystalline or non-liquid crystalline behaviours above their melting point. This depends both on the length of the alkylene spacers and on the type of mesogenic group. However, non-liquid crystalline bismaleimides can be converted into liquid crystalline bismaleimides by secondary reactions such as addition reactions, and can be further used as such.

Aliphatic maleimides can be homopolymerized by a radical mechanism, and can be polymerized with numerous other monomers, such as acrylates, methacrylates and vinyl compounds, such as styrene for example. Furthermore, the maleimide function enters into thermal, catalysed, uncatalysed and photochemical reactions with a multiplicity of other functional groups. Examples include the reactions thereof with glycidyl ethers, allyl ethers and esters, vinyl ethers, isocyano-esters, dithiols, diamines and phenylacetylenes. Compared with known liquid crystalline diacrylates, dimethacrylates, divinyl ethers and diglycidyl ethers, liquid crystalline bismaleimides thus exhibit a more versatile reaction behaviour, and in principle are thus outstandingly suitable for the synthesis of a multiplicity of LC networks.

According to the teaching of EP-A-0 847 991, maleimidocarboxylic acids can be produced in one step and in good yields from maleic anhydride and α,ω-aminocarboxylic acids. The α,ω-aminocarboxylic acids which are required therefore can be obtained industrially with different alkylene chain lengths between $(CH_2)_1$ and $(CH_2)_{20}$. Maleimidoalkylcarboxylic acids with alkylene chain lengths of $(CH_2)_3$ to $(CH_3)_{12}$ are the most preferred starting materials for the production of liquid crystalline crosslinking agents, since they already contain, in one molecule, a polymerisable or crosslinkable function and a spacer group of suitable and selectable chain length. Compared with methods known hitherto for the production of liquid crystalline crosslinking agents, this is a decisive advantage industrially.

The terminal carboxyl group of maleimidoalkylcarboxylic acids enables them to be reacted with a difunctional mesogen, in only one or at most two reaction steps, to form liquid crystalline crosslinking agents. Numerous reactions which are known in the art for the production of esters or acid amines are suitable for coupling maleimidoalkylcarboxylic acids to OH— or $NH_2$— functional mesogens, such as the reaction of acid chlorides with alcohols or amines in the presence of an acid scavenger, transesterification, or condensation with the separation of water. One preferred method of producing bismaleimides according to the invention is the reaction of maleimidoalkylcarboxylic acid chlorides with OH-functional mesogens in the presence of basic acid scavengers. Bismaleimides according to the invention which comprise amide linkages can be produced analogously from $NH_2$-functional mesogens and maleimidoalkylcarboxylic acid chlorides. The requisite acid chlorides can be produced, in a simple synthesis which proceeds to completion, from maleimidoalkylcarboxylic acids by reaction with thionyl chloride, sulphuryl chloride or oxalyl chloride, wherein thionyl and oxalyl chlorides are preferred.

Examples of suitable maleimidocarboxylic acids, to which the present invention is not exclusively restricted, however, include maleimidoacetic acid, maleimidopropionic acid, maleimidobutyric acid, D- and L-maleimidoisobutyric acids, maleimidocaproic acid, maleimidoheptanoic acid, maleimidononanoic acid, maleimidoundecanoic acid, maleimidododecanoic acid, 2-methylmaleimidocaproic acid, 2-methylmaleimidoundecanoic acid, 2,3-dimethylmaleimidobutyric acid and 2,3-dimethylmaleimidoundecanoic acid, wherein bismaleimides of long chain maleimidoalkylcarboxylic acids exhibit better liquid crystalline properties.

These maleimidoalkylcarboxylic acids can be converted into their acid chlorides, in a simple manner and in quantitative yields, with thionyl chloride, sulphuryl chloride, phosphorus pentachloride, phosphorus oxychloride or oxalyl chloride, wherein thionyl and oxalyl chloride are preferred, in suitable solvents, advantageously in halogenated hydrocarbons such as dichloromethane, chloroform, 1,1,2-trichloroethane or 1,1,2,2-tetrachloroethane, at temperatures of 0 to 100° C., preferably 0 to 70° C., optionally in the presence of acid scavengers such as tertiary amines or pyridine. These acid chlorides can be converted into bismaleimides according to the invention by their reactions, which are known in the art, with aromatic mesogens M corresponding to general structure (III) as shown below, with the formation of ester or amide bonds, wherein ester bond linkages are preferred:

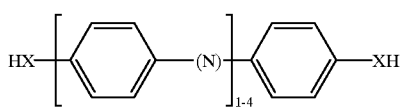
(III)

where X=—O or —NH; and if N is present: N=—COO—, —CONH—, —CH=CH—, —C(CH$_3$)=CH—, —C≡C—, —N=N—, N(O)=N—, CH=N— or —CH=N—N=CH—.

The mesogens M must contain two OH or NH$_2$ groups which are reactive with acid chlorides and must contain at least two aromatic rings which are linked para to each other by single, double or triple C—C bonds or by azo, azoxy, ester, amide, azomethine or azine groups, and which can be mono- or di-substituted in any position by alkyl groups or halogen atoms. An aromatic ring can be replaced by a heterocyclic ring, such as pyrimidine or 1,3-dioxane. Examples of mesogens which are suitable for the formation of bismaleimides according to the invention are the following:

4,4'-dihydroxybiphenyl, 4,4''-dihydroxyterphenyl, 4,4'-dihydroxydiphenyl-acetylene, 4,4'-dihydroxystilbene, 4,4'-dihydroxymethylstilbene, 4,4'-dihydroxy-azobenzene, 4,4'-dihydroxyazoxybenzene, 4-hydroxyphenyl-4-hydroxybenzoate, 4-aminophenyl-4-aminobenzoate, hydroquinone-bis-(4-hydroxybenzoate), 2-methyl-hydroquinone-1,4-bis-(4-hydroxybenzoate), bi-phenylyl-4,4'-bis-(4-hydroxybenzoate), 1,4-naphthylene-bis-(4-hydroxybenzoate), 1,5-naphthylene-bis-(4-hydroxybenzoate), 4,4'-dihydroxydiphenylazomethine, 4,4'-dihydroxydiphenylazine, 2-(4-hydroxyphenyl)-5-hydroxypyrimidine, 2-(4-hydroxyphenyl)-5-hydroxy-1,3-dioxane, and N,N-terephthalylidene-bis(4-hydroxybenzene).

The mesogens which are particularly preferred for the production of bismaleimides which crosslink above 100° C. with the formation of liquid crystalline phases are 4-hydroxyphenyl-4-hydroxybenzoate, hydroquinone-bis(4-hydroxybenzoate), 2-methylhydroquinone-1,4-bis(4-hydroxybenzoate) and diphenylyl-4,4'-bis(4-hydroxybenzoate). These mesogens can be produced from inexpensive compounds in a simple manner and in one step, even on a large scale, according to the teaching of the DE-OS 3622611 or as described by F. N. Jones et al. [Polym. Preprints ACS, 30(2), 462 (1989)], and are therefore particularly suitable for the commercial production of bismaleimides according to the invention.

Bismaleimides of general structure 1 in which X represents an ether linkage can also be produced. Thus ω-haloalkylmaleimides, preferably ω-bromoalkylmaleimides comprising 1 to 20, preferably 3 to 12, CH$_2$ groups which are linked linearly to each other, and which may also contain a chiral centre obtained by alkyl substitution, preferably by methyl substitution, can be linked to form bismaleimides by methods comprising Williamson ether synthesis under mild reaction conditions with the aromatic para-hydroxy-substituted mesogens cited above by way of example.

Therefore, the present invention further relates to a method of producing bismaleimides of formula (I), wherein X represents —O—, in which 2 equivalents of a halogenated N-alkylmaleimide of general formula

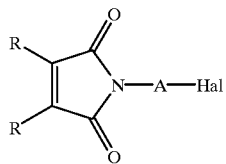

wherein R and A are as defined above and Hal represents a halogen atom, are reacted with a compound of general formula

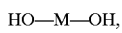

wherein M is defined as above, in a suitable solvent, in the presence of a catalyst or an acid acceptor, and at a temperature of 20 to 200° C., preferably 50 to 150° C., and the bismaleimides are isolated.

ω-haloalkylmaleimides can be obtained from ω-hydroxyalkylmaleimides by reaction with a halogenating agent such as PX$_3$, POX$_3$ or PX$_5$, wherein X represents Cl or Br. Another method of producing the desired ω-haloalkylmaleimides is the reaction of an alkali metal salt of maleinimide or of 7-oxabicycloheptene-1,2-dicarboxylic acid imide, which can be obtained in a simple manner by the Diels-Alder reaction of furane with maleinimide, with an excess of an α,ω-dihaloalkane, wherein α,ω-dibromoalkanes comprising 3 to 12 CH$_2$ groups are preferred. The desired ω-haloalkylmaleimides can be isolated from the reaction mixture by filtering off the alkali metal halide and preferably by removing the excess of α,ω-dihaloalkane by distillation, wherein the furane is also removed when 7-oxabicycloheptene-1,2-dicarboxylic acid imide is used.

The reaction of the ω-haloalkylmaleimides, which are produced in this manner, with para-substituted OH-functional mesogens of general formula (III) is advantageously conducted in the presence of dry K$_2$CO$_3$ in a dipolar aprotic solvent, such as acetone, cyclopentanone, cyclohexanone or dimethylformamide, wherein acetone is preferred, with the addition of a catalytic amount of potassium iodide.

Alternatively, bismaleimides of general formula (I) according to the invention, wherein X represents —O—, can be produced by method in which (i) a compound of general formula HO—M—OH, wherein M is as defined above, is reacted with 2 equivalents of an α,ω-haloalkane nitrile of general formula

wherein Hal represents a halogen atom and A' represents an alkylene chain comprising 2 to 19 CH$_2$ groups, and wherein one C atom of each alkylene chain A' can be chiral due to alkyl substitution, in a suitable aprotic dipolar solvent, in the presence of a catalyst and/or of an acid acceptor, and at a temperature of 20 to 200° C., preferably 50 to 150° C., to form an α,ω-dinitrile of general formula

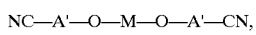

wherein A' and M are as defined above, (ii) the α,ω-dinitrile is reduced with a complex metal hydride in the presence of a strong acid with subsequent hydrolysis to form the corresponding α,ω-diamine of general formula

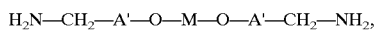

H₂N—CH₂—A'—O—M—O—A'—CH₂—NH₂, wherein A' and M are as defined above, and (iii) the α,ω-diamine is imidised with two equivalents of a maleic anhydride of general formula

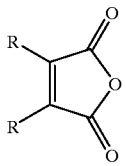

wherein R is as defined above, in a mixture consisting of an aliphatic carboxylic acid and an aromatic hydrocarbon at a temperature of 100 to 180° C., with the separation of water, to form the liquid crystalline bismaleimides.

In this method, the Williamson ether synthesis described above is first effected between the aforementioned exemplary aromatic para-hydroxy-substituted mesogens and 2 equivalents of an α,ω-haloalkane nitrile, preferably in the presence of dry K₂CO₃ in a dipolar aprotic solvent, such as acetone, cyclopentanone, cyclohexanone or dimethylformamide for example, wherein acetone is preferred, with the addition of a catalytic amount of potassium iodide, within the temperature range from 20 to 200° C., preferably 50 to 150° C. The α,ω-haloalkane nitriles which are preferably used are α,ω-bromoalkane nitriles comprising 3 to 12 CH₂ groups, one of which may be chiral due to alkyl substitution, preferably methyl substitution. The nitrile groups are then reduced to amines by methods known in the art, e.g. by reduction with complex metal hydrides in the presence of a strong acid, by LiAlH₄/H₂SO₄ for example, as described by N. M. Yoon and H. C. Brown in J. Am. Chem. Soc. 90, 2927 (1968). The diamines which are thus obtained are then reacted with equivalent amounts of unsubstituted or substituted maleic anhydride by methods of cyclisation which are likewise known, for example by heating in aliphatic carboxylic acids with the azeotropic removal of water by an aromatic entraining agent according to the teaching of EP-A-0 847 991, to form bismaleimides according to the invention which comprise ether linkages.

Bismaleimides according to the invention which comprise ether linkages can also be produced from diamines and maleic anhydride by the method described by C. Koβmehl, H.- I. Nagel and A. Phal in Agnewandte Makromolekulare Chemie 227, 139–57 (1995), wherein two equivalents of maleic anhydride are reacted with one equivalent of a diamine in dimethylformamide in the presence of one equivalent of acetic anhydride and of a catalyst constituting of nickel(II) acetate and triethylamine, at temperatures of 90 to 105° C., to form aliphatic bismaleimides.

The melting temperatures and the occurrence of liquid crystalline behaviour on melting, which can be observed under the polarising microscope in the form of multi-coloured textures which are generally nematic, depends on the length of the alkylene spacers and on the type of linking between the alkylene spacers and the mesogenic group, and also depends on the type of mesogenic group used. In general, bismaleimides comprising alkylene spacers with fewer than 3 CH₂ groups are not liquid crystalline. The more para-linked rings which are present in the mesogenic group, the more is liquid crystalline behaviour to be anticipated at average alkylene spacer lengths between (CH₂)₅ and (CH₂)₁₀. Thus bismaleimides comprising (CH₂)₅ and (CH₂)₁₀ chains and only two para-substituted benzene rings do not yet exhibit liquid crystalline properties. Furthermore, the occurrence of liquid crystallinity also depends on the mutual interactions of the mesogenic groups in the melt.

Since the bismaleimides according to the invention, which are of particular interest commercially since they can be obtained from simple precursors, either do not exhibit liquid crystalline behaviour or only have very narrow LC temperature ranges above 100° C. which limit their suitability for the formation of liquid crystalline networks to relatively narrow ranges of crosslinking temperatures, a further object of the present invention was to modify the bismaleimides according to the invention, by reactions which are as simple as possible and which as far as possible proceed to completion, so that their liquid crystalline transition range becomes wider or so that liquid crystallinity occurs anyway.

Therefore, the present invention also relates to oligomeric liquid crystalline bismaleimides of general formula (II)

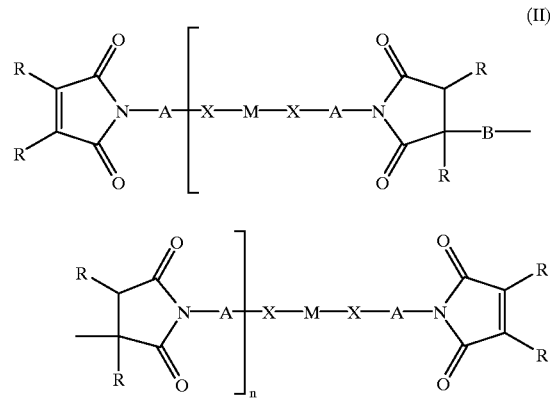

wherein A, X, M and R are as defined above, n represents an integer from 1 to 100 and B represents piperazinyl or a divalent radical which is derived from a primary or secondary para-substituted cyclic diamine, wherein B is bonded via the amino groups of the diamine.

The oligomeric liquid crystalline bismaleimides of general formula (II) according to the invention are produced from liquid crystalline bismaleimides of general formula (I) by the oligomerisation thereof by a Michael addition, in a suitable solvent, with half to one equivalent of a para-substituted aromatic, alicyclic or heterocyclic primary or secondary amine at a temperature of 0 to 80° C., preferably 20 to 50° C., and the reaction products are isolated by methods known in the art.

In this reaction, what are termed aspartimide linkages are formed between the diamines and the bismaleimides of general formula (I).

The bismaleimides of general formula (I) which are preferably reacted are those in which the maleimide double bonds comprise H atoms or one methyl group only.

The choice of solvent is not critical. Halogenated hydrocarbons, tertiary amides and ethers can be used for example, as well as mixtures thereof.

Cyclic 1,4-diamines are preferably used in the method according to the invention of producing oligomeric liquid crystalline bismaleimides. Examples thereof include p-phenylenediamine, 4,4'-diaminobiphenyl, 4,4'-diamino-3,3',5,5'-tetramethyl-biphenyl and N,N'-dimethyl-p-phenylenediamine.

Oligomeric compounds of this type can be described in terms of general structure IV:

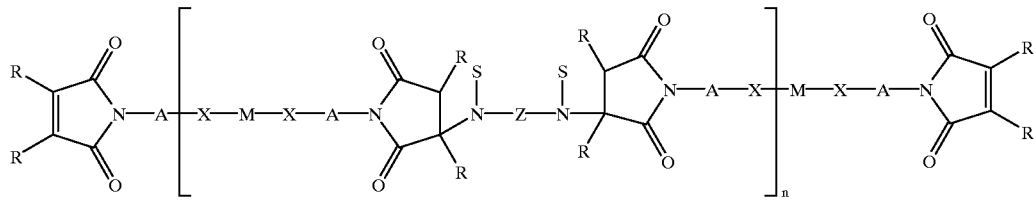

where Z=1,4-phenylene or 4,4'-biphenylene, and S=—H or —CH$_3$, wherein A, M, R and X have the same meanings as described for structure (I) and n denotes an integer between 1 and 100.

The reaction of bismaleimides with piperazine is particularly preferred, and results in liquid crystalline bismaleimides of general structure (V):

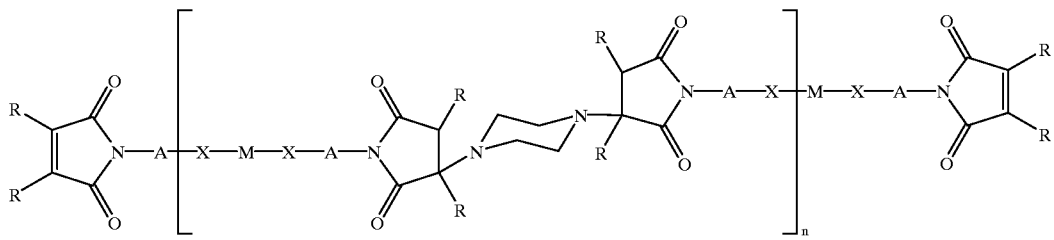

where A, M, R ad X have the same meanings as those described for structure (I) and n denotes an integer between 1 and 100.

The reaction of bismaleimides according to the invention with half an equivalent of a cyclic diamine essentially results in bisaspartimides with n=1, wherein oligomers with N>1 can still be formed, depending on the temperature of reaction.

In contrast, the reaction of one equivalent of a cyclic diamine with a bismaleimide results in oligomers with n>1. In cases such as these, where the mixtures obtained are soluble in CHCl$_3$ or tetrahydrofuran, chromatographically separated individual products are obtained by gel permeation chromatography which comprise 1 to 10 repeating units and a proportion of higher polymers with molecular weights up to >20,000 g/mole. On average, both types of product comprise two terminal maleimide groups per oligomer molecule, which are available for further reaction.

Chain extension of bismaleimides according to the invention with diamines, wherein piperazine is preferred, results in a plurality of significant improvements in properties. Thus the liquid crystalline temperature range, even for bisaspartimides (n=1), is for the most part considerably broadened compared with the corresponding bismaleimides. Thus the bismaleimide formed from 2 moles of maleimidohexanoic acid chloride and one mole of hydroquinone-bis(4-hydroxybenzoate) exhibits a nematic phase under the polarising microscope between 125 and 140° C., whilst the reaction product thereof with one mole of piperazine exhibits a nematic phase between 100 and about 325° C. Similar broadenings of the liquid crystalline temperature range are also observed for other LC bismaleimides and are due to an increase in the typical length/diameter ratio of the liquid crystalline bismaleimides. In this connection, the liquid crystalline temperature ranges also depend on the temperature of formation of the polyaspartimides, since in the upper region of the given reaction temperature range more products of higher molecular weight are formed, the mesogenic phases of which occur at higher temperatures than those which are produced at room temperature.

A characteristic of all low and high molecular weight bismaleimides according to the invention is their capacity for thermal crosslinking at temperatures above 200° C., which is due to thermal crosslinking bis maleimide groups. Depending on the mesogen used and on the alkylene spacer length, crosslinking may either occur in the mesogenic phase or may first occur in the isotropic phase above the clear point. If para-substituted primary aromatic diamines are used for chain extension, the more weakly basic secondary amino groups of the aspartimide groups can also react with the maleimide double bonds by a Michael addition at higher temperatures above 150° C. Piperazine-modified products are therefore preferred in many cases. In each case, liquid crystalline compounds are present which are capable of thermal crosslinking.

It is also of considerable practical importance that liquid crystalline properties are imparted by this modification even to those bismaleimides which do in fact contain mesogenic groups but which still do not exhibit liquid crystalline behaviour. Thus, for example, 4,4'-biphenyl-bis(oxycarbonylpentylmaleimide) itself does not exhibit a liquid crystalline transition, but merely exhibits a melting point at 110° C., wherein the melt remains isotropic under the polarising microscope. In contrast, the oligomeric reaction product with half an equivalent of piperazine exhibits, after isolation, a broad melting range up to 114° C. and moreover exhibits a nematic texture. The isolated oligomeric product from the reaction with one equivalent of piperazine exhibits a transition from the crystalline phase to the nematic phase at 79° C. and has a clear point of 180° C.

The solubility of piperazine-modified bismaleimides in many organic solvents is also better than that of bismaleimide starting materials, which is important for many applications.

The present invention embraces a liquid crystalline medium for electro-optical display, which comprises one or more than one mesogenic-group-containing bismaleimide and/or oligomeric bismaleimide obtained by oligomerization of the mesogenic-group-containing bismaleimide according to the present invention. The liquid crystalline medium for electro-optical display of the present invention may contain, as the one or more than one bismaleimide and/or oligomeric bismaleimide according to the present invention, at least one compound selected from the group of conventionally known liquid crystalline compounds within an extent not impairing the advantages of the present invention such as liquid crystallinity.

Specific examples of the conventionally known liquid crystalline compound include biphenyl compounds, terphenyl compounds, phenyl or cyclohexyl benzoate compounds, phenyl or cyclohexyl cyclohexanecarboxylate compounds, phenyl or cyclohexyl cyclohexexylbenzoate compounds, phenyl or cyclohexyl cyclohexylcyclohexanecarboxylate compounds, cyclohexylphenyl benzoate compounds, cyclohexylphenyl cyclohexanecarboxylate compounds, cyclohexylphenyl cyclohexylcyclohexanecarboxylate compounds, phenylcyclohexane compounds, cyclohexylbiphenyl compounds, phenylcyclohexylcyclohexane compounds, cyclohexylcyclohexane compounds, cyclohexylcyclohexene compounds, cyclohexylcyclohexylcyclohexene compounds, 1,4-bis-cyclohexylbenzene compounds, 4,4'-bis-cyclohexylbiphenyl compounds, phenyl- or cyclohexyl-pyrimidine compounds, phenyl- or cyclohexylpyridine compounds, phenyl- or cyclohexyldioxane compounds, phenyl- or cyclohexyl-1,3-dithian compounds, 1,2-diphenylethane compounds, 1,2-dicyclohexylethane compounds, 1-phenyl-2-cclohexylethane compounds, 1-cyclohexyl-2-(4-phenylcyclohexyl)ethane compounds, 1-cyclohexyl-2-biphenylethane compounds, 1-phenyl-2-cyclohexylphenylethane compounds and tolan compounds and fluorinated compounds thereof. Since the above-exemplified compounds differ in melting point and liquid crystallinity, a liquid crystalline composition suited for various liquid crystalline media can be prepared using a plurality of them in combination.

Bismaleimides according to the invention and aspartimide oligomers thereof are capable of forming liquid crystalline networks in solution or in the melt by crosslinking, either purely thermally or with radical initiators. When used as additives in amounts of 5–50% by weight, commercially available aromatic bismaleimide resins give rise to an improvement in the mechanical properties, primarily the toughness, of the cured products. They can also form liquid crystalline networks in combination with other unsaturated monomers, oligomers and reactive polymers.

The synthesis and properties of bismaleimides according to the invention can be demonstrated by means of the following examples.

EXAMPLE 1

Hydroquinone-bis (maleimidopentylcarbonyloxybenzoate)

7.0 g (0.02 mole) hydroquinone-bis(4-hydroxybenzoate) were dissolved, with stirring and under $N_2$, in a mixture of 70 g dimethylformamide and 6.9 g triethylamine, in a 100 ml round bottomed flask fitted with a magnetic stirrer bar and an $N_2$ gas inlet tube. The mixture was cooled on an ice bath to 0 to 5° C. and 11.4 g (0.05 mole) maleimidohexanoic acid chloride was added dropwise over 40 minutes. The batch was subsequently stirred for a further 15 hours at room temperature, the turbid, solids-containing mixture was filtered off and the filtrate was stirred into in 900 ml $H_2O$. The resulting colourless solid was recrystallised from 200 ml toluene/ethanol (1:1).

Yield: 8.25 g=56% theoretical.

Under a polarising microscope equipped with a hot stage the substance exhibited a melting point of 125° C. with the formation of a nematic texture and a clear point of 140° C.

EXAMPLE 2

Hydroquinone-bis (maleimidodecylcarbonyloxybenzoate)

7.0 g (0.02 mole) hydroquinone-bis(4-hydroxybenzoate) were dissolved, with stirring and under $N_2$, in a mixture of 70 g dimethylformamide and 6.9 g triethylamine, in a 100 ml round bottomed flask fitted with a magnetic stirrer bar and an $N_2$ gas inlet tube. The mixture was cooled on an ice bath to 0 to 5° C. and 15 g (0.05 mole) maleimidoundecanoic acid chloride dissolved in 50 ml dimethylformamide was added drop-wise over 40 minutes. The batch was subsequently stirred for a further 15 hours at room temperature, the turbid, solids-containing mixture was filtered off and the filtrate was stirred into 900 ml methanol. The resulting colourless solid was washed with 300 ml methanol and brief overnight under vacuum.

Yield: 14.00 g=80% theoretical.

Under the polarising microscope a sample of the compound from example 2 exhibited a melting point of 105° C. and a clear point of 130° C.

EXAMPLE 3

2-methylhydroquinone-bis (maleimidopentylcarbonyloxybenzoate)

1.4 g (3.8 mmole) 2-methylhydroquinone-bis(4-hydroxybenzoate) were dissolved, with stirring and under $N_2$, in a mixture of 30 g dimethylformamide and 0.9 g triethylamine, in a 50 ml round bottomed flask fitted with a magnetic stirrer bar and an $N_2$ gas inlet tube. The mixture was cooled on an ice bath to 0 to 5° C. and 2.0 g (8.6 mmole) maleimidohexanoic acid chloride was added drop-wise over 10 minutes. The batch was subsequently stirred for a further 15 hours at room temperature, the turbid, solids-containing mixture was filtered off and the filtrate was poured into 500 ml of iced water with stirring. In the course of this procedure, a white glutinous precipitate was deposited on the wall of the glass beaker. After removing the aqueous phase by decantation, the precipitate was embrittled with liquid $N_2$, comminuted, recrystallised from 200 ml methanol and dried under vacuum. $^1H$ and $^{13}C$ NMR spectra confirmed the formation of the desired product.

Yield: 2.85 g=95% theoretical.

Under the polarising microscope, a sample of the compound from example 3 exhibited a melting point of 91° C. and the subsequent formation of a nematic texture. The nematic melt solidified at 230° C. without a clear point becoming visible.

EXAMPLE 4

4,4'-biphenylyl-bis(maleimidohexyl ester)

4.3 g (0.023 mole) 4,4'-dihydroxybiphenyl were dissolved, with stirring and under $N_2$, in a mixture of 55 g dimethylformamide and 5.5 g triethylamine, in a 100 ml round bottomed flask fitted with a magnetic stirrer bar and an $N_2$ gas inlet tube. The mixture was cooled on an ice bath to 0 to 5° C. and 12.0 g (0.052 mole) maleimidohexanoic acid chloride was added drop-wise over 45 minutes. The batch was subsequently stirred for a further 45 hours at room temperature, and the turbid, solids-containing mixture was stirred into 900 ml of iced water. The resulting yellow precipitate was washed with water and recrystallised from 200 ml methanol, 1.5 g of insoluble residue being filtered off hot. A total of 6.2 g of recrystallised product was isolated and was recrystallised again from methanol, with the bulk of the first crystallised product remaining undissolved. Since this residue only exhibited a weak OH band in its IR spectrum at 3400 cm$^{-1}$, the product was recrystallised a third time from 50 ml methanol. After isolation and drying under vacuum, 1.6 g of the desired product were isolated, which had a purity of 95% as determined by NMR and liquid chromatography.

The yield of 95% of the target product corresponded to 12.0% theoretical.

The corresponding monoester, which was also a contaminant in the desired product, was dissolved in the filtrates from the first and second crystallisation steps.

Under the polarising microscope a sample of the third recrystallised product exhibited a melting point of 110° C. and formed an isotropic melt above that temperature.

EXAMPLE 5

Piperazine-bisaspartimide of hydroquinone-bis (maleimidopentylcarbonyloxybenzoate)

1.47 g (2 mmole) of the compound from example 1 were dissolved in 10 ml of dry dimethylformamide and 0.086 g (1 mmole) of solid piperazine were added. The batch was subsequently stirred for 15 hours at room temperature. Thereafter, the solution was poured on to 100 ml of iced water, and the precipitate was filtered off, washed with 50 ml water and dried under vacuum.

The yield was 1.22 g=78.3% theoretical.

$^1$H- and $^{13}$C NMR spectra confirmed the formation of an aspartimide comprising two terminal maleimide groups.

Under the polarising microscope a sample of the compound from example 5 exhibited a melting point of 80° C. and formed an anisotropic melt with a nematic texture, which became isotropic at 130 to 135° C.

EXAMPLE 6

Piperazine-polyaspartimide of hydroquinone-bis (maleimidopentylcarbonyloxybenzoate)

1.47 g (2 mmole) of the compound from example 1 were dissolved in 10 ml of dry dimethylformamide and 0.172 g (2 mmole) of solid piperazine were added. The batch was subsequently stirred for 15 hours at room temperature. Work-up was as described in example 5.

The yield was 1.42 g=86.4% theoretical.

NMR spectra confirmed the desired aspartimide structure. Under the polarising microscope a sample of the compound from example 6 exhibited a melting point of 100° C. and formed an anisotropic melt, the nematic texture of which changed at 125° C. and which became isotropic and solidified at 320° C.

EXAMPLE 7

Piperazine-polyaspartimide of hydroquinone-bis (maleimidopentylcarbonyloxybenzoate)

1.47 g (2 mmole) of the compound from example 1 were dissolved in 10 ml of dry dimethylformamide and 0.172 g (2 mmole) of solid piperazine were added. The batch was subsequently stirred for 24 hours at 60° C. Work-up was as described in example 5.

The yield was 1.02 g=53.1% theoretical.

NMR spectra confirmed the desired aspartimide structure. Under the polarising microscope a sample of the compound from example 7 exhibited a melting point of 160° C. and formed an anisotropic melt with a nematic texture, which solidified anisotropically at 300° C.

EXAMPLE 8

1,4-phenylene-bisaspartimide of hydroquinone-bis (maleimidopentylcarbonyloxybenzoate)

0.736 g (1 mmole) of the compound from example 1 were dissolved in 10 ml of dry dimethylformamide and 0.054 g (1 mmole) 1,4-phenylenediamine were added. The batch was stirred for 19 hours at room temperature. Work-up was as described in example 5.

The yield was 0.57 g=72.2% theoretical.

NMR spectra confirmed the desired aspartimide structure. Under the polarising microscope a sample of the compound from example 8 exhibited a melting point of 115° C. and formed a anisotropic melt, the nematic texture of which changed at 150° C. and which became isotropic and solidified at 250° C.

EXAMPLE 9

1,4-phenylene-polyaspartimide of hydroquinone-bis (maleimidopentylcarbonyloxybenzoate)

0.736 g (1 mmole) of the compound from example 1 were dissolved in 10 ml of dry dimethylformamide and 0.108 g (1 mmole) 1,4-phenylenediamine were added. The batch was stirred for 19 hours at room temperature. Work-up was as described in example 5.

The yield was 0.48 g=56.9% theoretical. NMR spectra confirmed the desired aspartimide structure.

Under the polarising microscope a sample of the compound from example 9 exhibited a melting point of 122° C. and formed an anisotropic melt, the nematic texture of which changed at 190° C. and which became isotropic and solidified at 350° C.

EXAMPLE 10

Piperazine-bisaspartimide of hydroquinone-bis (maleimidodecylcarbonyloxybenzoate)

0.877 g (1 mole) of the compound from example 2 were dissolved in 5 ml dry dimethylformamide and 0.043 g (0.5 mmole) piperazine were added. The batch was stirred for 15 hours at room temperature. Work-up was as described in example 5. The yield was 0.73 g=79.3% theoretical. NMR spectra confirmed the desired aspartimide structure. Gel chromatography in CHCl$_3$ using a polystyrene calibration standard (400–800,000 g/mole) showed that a mixture of about 80% bisaspartimide was present in addition to about 20% of bismaleimide.

Under the polarising microscope a sample of the compound from example 10 exhibited a melting point of 100° C. and formed an anisotropic melt with a nematic texture, which became isotropic at 118° C.

EXAMPLE 11

Piperazine-polyaspartimide of hydroquinone-bis (maleimidodecylcarbonyloxybenzoate)

0.877 g (1 mmole) of the compound from example 2 were dissolved in 5 ml dry dimethylformamide and 0.086 g (1 mmole) piperazine were added. The batch was stirred for 15 hours at room temperature. Work-up was as described in example 5. The yield was 0.76 g=78.6% theoretical. NMR spectra confirmed the desired aspartimide structure. Gel chromatography in $CHCl_3$ using a polystyrene calibration standard (400–800,000 g/mole) showed a mixture of oligomers comprising 1–12 repeating units and a small amount of higher polymers with molecular weights >20,000 g/mole.

Under the polarising microscope a sample of the compound from example 11 exhibited a melting point of 105° C. and formed an anisotropic melt with a nematic texture, which became isotropic at 130° C.

EXAMPLE 12

Piperazine-bisaspartimide of biphenylylbis (maleimidohexyl ester)

0.67 g (1.2 mmole) of the compound from example 4 were dissolved in 5 ml dry DMF and treated with 0.051 g (0.6 mmole) of solid piperazine. The batch was stirred for 15 hours at 70° C. After cooling, the turbid solution was filtered and was added drop-wise to 70 ml of iced water. The resulting precipitate was washed with 100 ml water, isolated and dried under vacuum. The yield was 0.6 g=82.7% theoretical. NMR spectra confirmed the desired aspartimide structure. Under the polarising microscope a sample of the compound from example 12 exhibited a broad melting range and above 114° C. formed an anisotropic melt with a nematic texture, which solidified at about 240° C.

EXAMPLE 13

Piperazine-polyaspartimide of biphenylyl-bis (maleimidohexyl ester)

0.3 g (0.5 mmole) of the compound from example 4 were dissolved in 5 ml of dry $CH_2Cl_2$ together with 0.045 g (0.5 mmole) piperazine and were stirred for 4 hours at room temperature. After the removal of the solvent, the solid residue was stirred with 20 ml water, filtered off and dried under vacuum. The yield was 0.3 g=87% theoretical. NMR spectra confirmed the desired aspartimide structure.

Under the polarising microscope a sample of the compound from example 13 exhibited a melting point of 79° C. and formed an anisotropic melt with a nematic texture, which became isotropic and solidified at 180° C.

EXAMPLE 14

Piperazine-bisaspartimide of 2-methylhydroquinone-bis(maleimido-pentylcarbonyloxybenzoate)

1.00 g (1 mmole) of the compound from example 3 were dissolved in 10 ml of dry $CH_2Cl_2$ together with 0.045 g (0.5 mmole) piperazine and were stirred for 4 hours at room temperature. After the removal of the solvent, the solid residue was stirred with 50 ml water, filtered off and dried under vacuum. The yield was 0.90 g=86% theoretical. NMR spectra confirmed the desired aspartimide structure. Gel chromatography in THF using a polystyrene calibration standard (400–800,000 g/mole) showed that a bisaspartimide with a molecular weight of 1600 g/mole had been formed as the main product, in addition to which there were oligomers present which had molecular weights up to 4500 g/mole.

Under the polarising microscope a sample of the compound from example 14 exhibited a melting point of 92° C. and formed an anisotropic melt with a nematic texture, which became isotropic at 134° C.

EXAMPLE 15

Piperazine-polyaspartimide of 2-methylhydroquinone-bis (maleimidopentylcarbonyloxybenzoate)

0.25 g (0.33 mmole) of the compound from example 3 were dissolved in 5 ml of dry $CH_2Cl_2$ together with 0.029 g (0.33 mmole) piperazine and were stirred for 4 hours at room temperature. After the removal of the solvent, the solid residue was stirred with 20 ml water, filtered off and dried under vacuum. The yield was 0.24 g=86% theoretical. NMR spectra confirmed the desired aspartimide structure. Gel chromatography in THF using a polystyrene calibration standard (400–800,000 g/mole) showed that the presence of a broad distribution of oligomers with molecular weights ranging up to 7000 g/mole.

Under the polarizing microscope a sample of the compound from example 15 exhibited a melting point of 96° C. and formed an anisotropic melt with a nematic texture, which became isotropic and solidified at 180° C.

Example 16: 4,4'-biphenylyl-bis(oxypentylmaleimide):
a) Synthesis of 4,4'-biphenylyl-bis(oxybutylronitrile)
9.3 (0.05 mole) 4,4'-dihydroxybiphenyl, 20.7 (0.15 mole) anhydrous $K_2CO_3$ and 0.5 g potassium iodide in 200 ml acetone were heated to reflux temperature and homogenized for 1 hour in a 500 ml round bottomed flask fitted with a magnetic stirred bar, a reflux condenser and a dropping funnel, and a solution of 16.2 g (0.1 mole) 5-bromovaleronitrile in 15 ml acetone was then added drop-wise over 15 minutes. The mixture was then boiled for 25 hours under reflux. After cooling, a further 100 ml acetone were added and the suspension was filtered under suction. The solid was washed with 600 ml $H_2O$, dried, and recrystallized from 100 ml $CHCl_3$. After drying under vacuum, the yield of recrystallized product was 14.1 g=81% theoretical M.p: 170° C. The NMR and mass spectra corresponded to the desired substance.

b: Synthesis of 4,4'-biphenylyl-bis(oxypentylamine):
8.1 g (0.21 mole) of powdered $LiAlH_4$ were suspended in 190 ml dry diethyl ether under $N_2$ in a 500 ml three-necked flask fitted with a reflux condenser, stirrer, dropping funnel and $N_2$ gas inlet tube and were cooled to 0 to 5° C. in an ice bath, followed by the careful drop-wise addition of 10.4 g (0.106 mole) of 96% $H_2SO_4$ over 40 minutes. The mixture was stirred for 1 hour in an ice bath and then 12.0 g (0.034 mole) 4,4'-biphenylyl-bis(4-oxybutylronitrile) in 150 ml $CH_2Cl_2$ were added drop-wise over 50 minutes. The batch was then heated for 1 hour under reflux and was stirred overnight at room temperature. The reaction mixture was subsequently treated dropwise, whilst being cooled in ice and whilst being vigorously stirred, with 53 ml $H_2O$. After the exothermic reaction had died down, a solution of 10.5 g (0.26 mole) NaOH in 95 ml $H_2O$ was rapidly added. Thereafter, the batch was filtered under suction and the filtrate was evaporated. The filter cake was extracted twice, hot, with 250 ml $CHCl_3$ each time and was filtered. The chloroform extracts were combined with the residue from evaporation and the solvent was completely removed under vacuum. The crystalline product was dried under vacuum at 50° C.

Yield: 9.5 g=78% theoretical.
M.p.:=132 to 134° C. The NMR and mass spectra corresponded to the desired substance. The purity was about 95% as determined by GC.

c) Synthesis of 4,4'-biphenylyl-bis(oxypentylmaleimide)
7.1 g (0.02 mole) 4,4'-biphenylyl-bis(oxypentylmaleimide) from example 16b were dissolved at room temperature in a mixture of 50 ml of anhydrous propionic acid and 30 ml xylene in a 100 ml round bottomed flask fitted with a water trap and a reflux condenser. 3.9 g (0.04 mole) maleic anhydride and 0.1 ml concentrated $H_2SO_4$ were added and the reaction mixture was boiled under reflux on an oil bath at a temperature of 170 to 175° C. for 5 hours, during which period 1.1 ml of a mixture of water and propionic acid was collected in the trap. A precipitate was formed on cooling, and after isolation was extracted hot with 50 ml chloroform. After the removal of the solvent and drying under vacuum there remained a colourless, crystalline product, the NMR spectra of which corresponded to the desired substance. Yield: 4.7 g=45.6% theoretical.
M.p.:=156 to 160° C. The substance exhibited no liquid crystalline behaviour under the microscope.
Example 17: Piperazine-bisaspartimide of 4,4'-biphenylyl-bis(oxypentylmaleimide):
0.5 g (0.97 mmole) of the compound from example 16 were dissolved in 11 ml of dry $CH_2Cl_2$ together with 0.042 (0.48 mmole) piperazine and the batch was stirred for 4 hours at room temperature. After the removal of the solvent the solid residue was stirred with 20 ml water, filtered off and dried under vacuum. The yield was 0.44 g=87% theoretical. The NMR spectra confirmed the desired aspartimide structure.
Under the polarising microscope a sample of the compound from example 17 exhibited a melting point of 130° C. and formed an anisotropic melt with a nematic texture, which solidified above 250° C.
Example 18: Piperazine-polyaspartimide of 4,4'-biphenylyl-bis(oxypentylmaleimide) 0.5 g (0.97 mmole) of the compound from example 16 were dissolved in 11 ml of dry $CH_2Cl_2$ together with 0.0843 g (0.97 mmole) piperazine and the batch was stirred for 4 hours at room temperature. After the removal of the solvent the solid residue was stirred with 20 ml water, filtered off and dried under vacuum. The yield was 0.47 g=92.5% theoretical. The NMR spectra confirmed the desired aspartimide structure.
Under the polarising microscope a sample of the compound from example 18 exhibited a melting point of 115° C. and formed an anisotropic melt with a nematic texture, which became isotropic and solidified at 200° C.
Examples of synthesis of precursors of I.C. bismaleimides:
Maleimidohexanoic acid chlorine:
44.0 g (0.209 mole) maleimidohexanoic acid were dissolved in 250 ml of dry $CH_2Cl_2$ in a 500 ml round bottomed flask fitted with a stirrer, reflux condenser and $CaCl_2$ drying tube, and were treated with 34.8 g (0.29 mole) $SOCl_2$ and boiled under reflux for 3.5 hours. The $CH_2Cl_2$ was distilled off under normal pressure from the orange-coloured suspension which was thus obtained, and the $SOCl_2$ was subsequently distilled off at 80 mbar. After the addition of 0.1 g phenothiazine as a polymerization inhibitor, the dark-coloured residue was then subjected to fractional distillation via a 20 cm Vigreaux column. 15.2 g of a first fraction were collected over a boiling range of 140 to 145° C./0.02 mbar. The oil batch temperature was subsequently increased to 190° C. and 7.4 g of a second fraction with the same boiling range were isolated. Both distillates crystallized rapidly at room temperature. As determined by GC/MS both fractions were identical and had a purity of 96–97% as determined by GC. Yield after distillation: 47.2% theoretical.
Maleimidoundecanoic acid chloride:
24.0 g (0.085 mole) maleimidoundecanoic acid were dissolved in 50 ml of dry $CH_2Cl_2$ in a 250 ml round bottomed flask fitted with a stirrer, reflux condenser and $CaCl_2$ drying tube, and were treated with 31.0 g (0.24 mole) oxalyl and boiled under reflux for 15 hours at an oil bath temperature of 70 to 75° C. Subsequently, the $CH_2Cl_2$ was first distilled off under normal pressure, and the oxalyl chloride was distilled off at 0.01 mbar. On account of its susceptibility to hydrolysis, the dark-coloured residue was not purified further, but was immediately used for further syntheses. Yield: 2.5 g=100% theoretical. The maleimidoundecanoic acid chloride had a purity of 94% as determined by GC/MS.
5-Bromopentylmaleimide:
12 g (0.124 mole) maleimide were dissolved in 60 ml ethyl acetate and 22.4 g (0.33 mole) distilled furane were added over 10 minutes, whereupon the mixture became slightly warm, and the batch was stirred for 25 hours at room temperature. The precipitate was subsequently filtered off under suction and was dried under vacuum at room temperature. Yield: 10.5 g=51.3% theoretical. The substance was pure as determined by GC and its IR, NMR and mass spectra corresponded to the desired 7-oxabicycloheptene-1,2-dicarboxylic acid imide. 10 g (0.06 mole) of this imide were is dissolved in 300 ml distilled DMF, an amount of KI which covered the tip of a spatula was added, and 8.1 g (0.072 mole) K-tert-butylate were added under $N_2$. After 2 hours 69.6 g (0.303 g) 1,5-dibromopentane in 100 ml DMF were added drop-wise over 7 hours with stirring and at room temperature. The batch was subsequently stirred for 50 hours at room temperature. The DMF solution was filtered from the precipitated KBr and the DMF was substantially removed by distillation in a rotary evaporator under vacuum. The liquid residue was distilled in a microdistillation apparatus under a vacuum of $1\times10^{-3}$ mbar, whereupon at a boiling temperature of 50–55° C. it was solely the excess 1,5-dibromopentane which distilled over. The temperature of the oil bath was then slowly raised to 140° C. After a preliminary flow of 2.3 g, 5.5 g product distilled over at a boiling temperature of 113° C./$3\times10^3$ mbar. This product was pure as determined by G C, and its IR, NMR and mass spectra corresponded to the desired 5-bromopentylmaleimide. Yield: 5.5 g=37.4%.
Synthesis of hydroquinone-bis(4-hydroxybenzoate) (according to F. N. Jones et al., Polym. Prepr. ACS, 30(12), 462(1989)):
A mixture of 35.8 g (0.325 mole) hydroquinone, 89.6 g (0.65 mole) 4-hydroxybenzoic acid, 0.2 g p-toluenesulphonic acid and 8 g Shellsol A (a mixture of aromatic hydrocarbons, boiling range 225 to 250° C.) was heated $N_2$ to 208° C. in a 250 ml three-necked flask fitted with a Dean and Stark water trap, a stirrer and an $N_2$-inlet tube, whereupon $H_2O$ distilled off azeotropically. After the theoretical amount of water of 11.8 ml had been formed, the batch was cooled, the solid brown residue was boiled twice in 500 ml methanol each time, and the hot suspension was filtered under suction and washed with copious amounts of hot methanol. The white product was dried under vacuum at 80° C. The yield was 99.2 g=86.8% theoretical. The NMR spectra corresponded to the desired compound. As observed under the polarising microscope, the melting point was 270° C. with the subsequent formation of a nematic phase.
2-methylhydroquinone-bis(4-hydroxybenzoate) was also produced from 0.5 mole 2-methylhydroquinone and 1 mole 4-hydroxybenzoic acid by the same method. Yield: 47.0 g=25.8% theoretical. The NMR spectra corresponded to the desired compound. As observed under the polarising microscope, the melting point was 250° C. with the subsequent formation of a nematic phase.

Example 19: 4,4'-biphenylyl-bis(oxypentylmaleimide)

2.0 g (0.011 mole) 4,4'-dihydroxybiphenyl, 4,4 g (0.032 mole) K₂CO₃ and 0.1 g KI were suspended in 80 ml dry acetone and heated for 7 hours under reflux. A solution of 6.6 g (0.026 mole) 5-bromopentylmaleimide in 80 ml acetone was then added drop-wise over 30 minutes and the batch was heated for 20 hours under reflux. After cooling, the mixture was cooled in a mixture of ice and common salt, and the precipitate which was formed was filtered off under suction. The acetone solution was evaporated to dryness and the residue was recrystallized from 50 ml chloroform. After drying under vacuum, there remained a colourless, crystalline product, the NMR spectra of which corresponded to the desired substance. Yield: 4.2 g=74.0% theoretical. M.p.:= 156–160° C.

(Example 20)

Preparation of Compound (1):

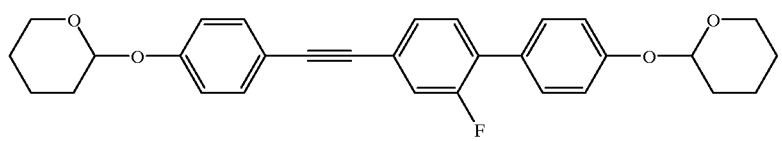

<Step 1>

Preparation of Compound (2):

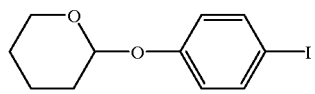

In a 300 ml eggplant type flask fitted with a thermometer and a dropping funnel, 4-iodophenol (29.0 g), paratoluene-sulfonic acid (9 mg) and dichloromethane (50 ml) were charged, followed by stirring over an ice bath to prepare a suspension. To the resulting suspension, 220 ml of a dichloromethane solution of 3,4-dihydropyrane (22.2 g) were added dropwise over about 1 hour while maintaining the temperature at not higher than 10° C.

The reaction mixture was then stirred at room temperature for about 4 hours under a nitrogen atmosphere. When the reaction mixture became a uniform brown solution, the progress of the reaction was checked by thin-layer chromatography or gas chromatography. After confirmation of the disappearance of the starting materials, the reaction was terminated. The reaction mixture was washed successively with a saturated aqueous solution of sodium bicarbonate and a saturated saline and then dried over anhydrous potassium carbonate. After the potassium carbonate was filtered off, the solvent was removed from the filtrate, whereby a crude product (47.2 g) was obtained. The crude product thus obtained was purified by silica gel chromatography (250 g of silica gel, hexane/dichloromethane=2/1 by volume) to yield a target product.

Yield: 37.1 g (93%).

¹³C-NMR(75 MHz, DMSO-d₆): δ(ppm)=18.391, 24.527, 29.618, 61.432, 84.182, 95.655, 119.039, 137.824, 156.338

<Step 2>

Preparation of Compound (3):

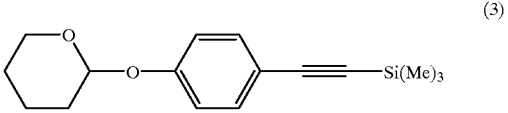

In a 1 liter four-necked flask fitted with a thermometer and an N₂ gas inlet tube, the compound (2) (60 g) and trimethylsilylacetylene (23.26 g) were weighted. The resulting mixture was dissolved in dimethylformamide (240 g) and triethylamine (70 g), followed by the addition of triphenylphosphine palladium (2.74 g) and copper iodide (0.75 g) as catalysts in a nitrogen atmosphere under cooling (25° C.) with water.

After the disappearance of the starting materials was confirmed by gas chromatography, the reaction was terminated. To the reaction mixture, 1 liter of ethyl acetate was added. The resulting mixture was washed 3 times with 500 ml of saturated saline and then dried over potassium carbonate. After potassium carbonate was filtered off, the solvent was removed from the filtrate, whereby a crude product was obtained. Yield: 61 g.

¹³C-NMR(75 MHz, DMSO-d₆): δ(ppm):=0.0004, 18.461, 24.555, 29.671, 61.567, 92.261, 95.627, 115.037, 116.419, 132.992, 156.902

<Step 3>

Preparation of Compound (4):

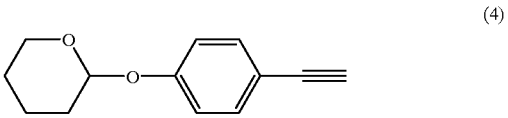

In a 300 ml three-necked flask fitted with an N₂ gas inlet tube, a thermometer and a dropping funnel, tetrabutylammonium fluoride (46 g) was weighted and it was dissolved in 65 g of dichloromethane. While maintaining the temperature at not higher than 10° C. over an ice bath in a nitrogen atmosphere, 100 ml of a dichloromethane solution of the compound (3) (34 g) were added dropwise to the resulting solution over 30 minutes. After completion of the dropwise addition, the reaction mixture was stirred at room temperature for about 3 hours. The progress of the reaction was checked by gas chromatography. After confirmation of the disappearance of the starting materials, the reaction was terminated.

The reaction mixture was washed twice with saturated saline and dried over anhydrous potassium carbonate. After the potassium carbonate was filtered off, the solvent was removed from the filtrate, whereby a crude product (70 g) was obtained. The crude product was purified by column chromatography (silica gel/dichloromethane), whereby a target product was obtained. Yield: 25 g.

$^{13}$C-NMR(75 MHz, DMSO-d$_6$): δ(ppm)=18.448, 24.551, 29.651, 61.555, 79.197, 83.367, 95.614, 114.531, 116.489, 133.021, 156.832

<Step 4>
Preparation of Compound (5):

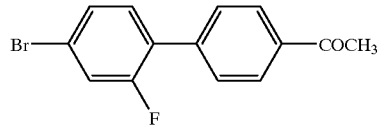

In a 1 liter four-necked flask fitted with a dropping funnel, a thermometer and a hydrogen chloride exhaust tube, aluminum chloride (32 g) was weighed and dispersed in 120 ml of dichloromethane by stirring. To the resulting dispersion, acetyl chloride (21 g) was added dropwise over 2 hours, followed by dropwise addition of 200 ml of a dichloromethane solution of 4-bromo-2-fluoro-1-phenylbenzene (50 g). About 4 hours later, the progress of the reaction was checked by gas chromatography.

To the starting materials which had remained unreacted, 4 g of acetyl chloride and 5 g of aluminum chloride were added further. Three hours later, the progress of the reaction was checked by gas chromatography again. After confirmation of the disappearance of the starting materials, the reactions was terminated. In a 1 liter beaker, about 500 g of crushed ice were charged, in which the reaction mixture was charged in portions. Aluminum chloride was completely inactivated by stirring the reaction mixture by a mechanical stirrer for about 30 minutes. The organic layer was washed twice with saturated saline and dried over anhydrous magnesium sulfate. The solvent was then removed, whereby a product was obtained. Yield: 57 g.

$^{13}$C-NMR(75 MHz, DMSO-d$_6$): δ(ppm)=26.706, 119.368, 119.713, 121.860, 126.622, 128.193, 128.456, 128.933, 132.198, 136.138, 138.474, 157.202, 160.533, 197.413

<Step 5>
Preparation of Compound (6):

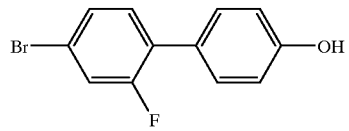

As a reactor, a 1 liter four-necked flask was used, while a magnetic stirrer was employed for stirring. The reactor was fitted with a thermometer and a Dimroth condenser. In the reactor, formic acid (750 ml) and the compound (5) (50 g) were weighed. While stirring the resulting mixture, aqueous hydrogen peroxide (34.5%, 50 ml) was added thereto, followed by reflux under heating by a mantle heater. About 12 hours later, the progress of the reaction was checked by gas chromatography. Since it was confirmed that a further decrease in the starting materials stopped, the reaction was terminated.

In a draft, the reaction mixture was ice cooled. A 10% aqueous solution of sodium bisulfide was added to the reaction mixture, which generated a large amount of a sulfur dioxide gas and decomposed the peroxide. Complete decomposition of the peroxide was checked using a potassium iodate starch paper. The reaction mixture was extracted twice with 500 ml of ethyl acetate. The organic layers were combined, followed by washing with water in repetition to adjust its pH to about 4. The organic layer was then neutralized by washing with a saturated aqueous solution of sodium bicarbonate. In the end, it was washed twice with saturated saline. After the organic layer was dried over anhydrous magnesium sulfate, the solvent was removed, whereby 50 g of a crude product were obtained. The resulting crude product was purified by column chromatography (500 g of alumina/toluene to ethyl acetate), whereby a target product was obtained. Yield: 30 g (70%).

<Step 6>
Preparation of Compound (7):

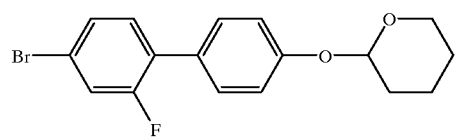

In a 200 ml two-necked flask fitted with a thermometer, a dropping funnel and an N$_2$ gas inlet tube, 4-(4-bromo-2-fluorophenyl)phenol (30 g), dichloromethane (50 ml) and paratoluenesulfonic acid (10 mg) were weighed. The resulting mixture was cooled over an ice bath and a dichloromethane solution (20 ml) of 3,4-dihydropyran (18.9 g) was added dropwise thereto over 30 minutes at a temperature maintained at not higher than 10° C. After completion of the dropwise addition, the reaction mixture was stirred at room temperature. The progress of the reaction was checked by gas chromatography. After confirmation of the disappearance of the starting materials, the reaction was terminated. The reaction mixture was then washed successively with a saturated aqueous solution of sodium bicarbonate and saturated saline and dried over anhydrous potassium carbonate. The solvent was then removed, whereby a crude product was obtained. The resulting crude product was purified by column chromatography (silica gel/hexane: toluene:dichloromethane=1:1:1 by volume), whereby a target product was obtained. Yield: 30.5 g.

<Step 7>
Preparation of Compound (1):

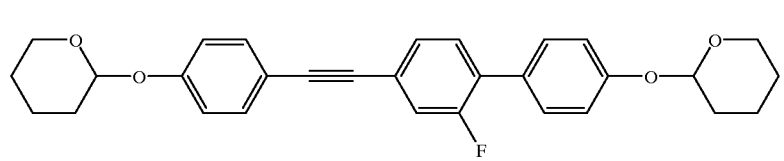

In a 1 liter four-necked flask fitted with an N$_2$ gas inlet tube, a Dimroth condenser and a thermometer, the compound (4) (20.7 g), the compound (7), (30g), 300 ml of dimethylformamide and 60 ml of triethylamine were weighed and they were stirred. To the reaction mixture, triphenylphosphine palladium (2.4 g) and copper iodide (0.98 g) were added as catalysts, followed by purging with a nitrogen gas. Reaction was effected for about 4 hours by heating the resulting <Step 9>

Preparation of Compound (9):

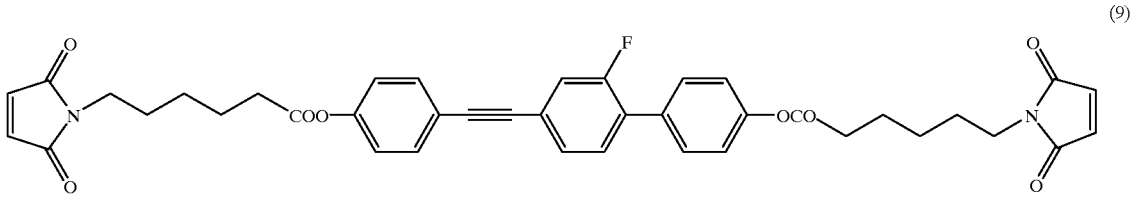

mixture to 90° C. by a mantle heater. The progress of the reaction was checked by a thin-layer chromatography. After confirmation of the disappearance of the starting materials, the reaction was terminated.

To the reaction mixture, 500 ml of toluene were added and the resulting mixture was washed 3 times with saturated saline. After the organic layer was dried over potassium carbonate, the solvent was removed, whereby a crude product was obtained. The resulting crude product was purified by column chromatography (silica gel/toluene), whereby a target product was obtained. Yield: 31 g.

$^{13}$C-NMR(75 MHZ, DMSO-d$_6$): δ(ppm)=18.662, 25.143, 30.194, 62.040, 87.077, 90.572 96.272, 115.823, 116.472, 118.710, 119.039, 123.747, 127.584, 12.440, 130.011, 130.241, 130.298, 133.037, 156.947, 157.350, 157.613, 160.887:

FT-IR(cm$^{-1}$):2940, 2880, 2850, 2210, 1600, 1540, 1510, 1400, 1350, 1280, 1200, 1180, 1110, 1040, 1020, 960, 920, 770, 830

<Step 8>
Preparation of Compound (8):

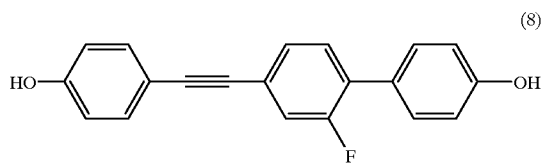

In a 500 ml four-necked flask fitted with a Dimroth condenser and a thermometer, the compound (1) (10 g) was weighed. To the compound, 100 ml of tetrahydrofuran were added to dissolve the former in the latter while heating by a drier. To the resulting solution, 10% hydrochloric acid (100 ml) was added, followed by stirring for about 30 minutes. After confirmation of the disappearance of the starting materials by thin-layer chromatography, the reaction was terminated.

To the reaction mixture, 500 ml of ethyl acetate were added and the resulting mixture was washed twice with saturated saline. After the organic layer was dried over magnesium sulfate, the solvent was removed, whereby a target product was obtained. The reaction yield was stoichiometric.

$^{13}$C-NMR(75 MHz, DMSO-d$_6$): δ(ppm)=86.221, 91.140, 111.957, 115.510, 115.782, 115.921, 118.109, 118.438, 122.649, 122.781, 124.821, 124.845, 127.576, 129.838, 130, 398, 157.556, 158.362, 160.188

FT-IR(cm$^{-1}$): 3400, 2360, 2200, 1900, 1650, 1610, 1550, 1510, 1490, 1440, 1410, 1370, 1320, 1250, 1180, 1100, 1010, 950, 870, 830, 820, 620, 590, 540

In a 50 ml three-necked flask fitted with a dropping funnel and a Dimroth condenser, 3.1 g (14.5 mmol) of maleimide-hexanoic acid were weighed under a nitrogen atmosphere and suspended in 20 ml of toluene. To the resulting suspension, 13.1 g (62.4 mmol) of trifluoroacetic anhydride were added to dissolve the latter in the former, followed by stirring for 30 minutes. To the reaction mixture, 2.0 g (6.6 mmol) of the compound (8) were added. The resulting mixture was heated over an oil bath and refluxed at 54° C. The reflux temperature showed a gradual increase and four hours later, it reached 58° C. After confirmation of the reaction by thin-layer chromatography, reflux was terminated.

The reaction mixture was neutralized with a saturated aqueous solution of sodium bicarbonate, while cooling over ice water bath. The neutralized mixture was extracted with ethyl acetate. The organic layer was washed 3 times with saturated saline and then dried over anhydrous sodium sulfate. The solvent was removed, whereby a crude product was obtained. The crude product was recrystallized from ethanol. The resulting crystals were washed with methanol and then dried under reduced pressure, whereby a target product was obtained. Yield: 2.5 g(56%).

$^{13}$C-NMR(300 MHz, CDCl$_3$): δ(ppm)=7.59–7.53 (4H), 7.44–7.29 (3H), 7.17 (2H), 7.10 (2H) 6.69 (4H), 3.56 (4H) 2.57 (4H), 1.85–1.62 (8H), 1.43 (4H):

$^{13}$C-NMR(75 MHz, CDCl$_3$): δ(ppm)=171.8, 171.6, 170.8, 160.9, 157, 150.8, 150.5, 134.1, 132.8, 130.6, 130.0, 128.3, 127.8, 124.0, 121.7, 121.8, 120.3, 119.3, 118.9, 90.0, 88.0, 37.6, 34.1, 28.2, 26.2, 24.3:

FT-IR(cm$^{-1}$): 3450, 3100, 2920, 2850, 1750, 1710, 1540, 1510, 1440, 1410, 1370, 1300, 1210, 1170, 1130, 1010, 950, 920, 840, 700:

DI-EI-MS (70 eV): m/z=690, 497, 469, 304, 110

Elemental analysis: C=69.2, H=5.2, N=3.8, Calculated (C=69.35, H=5.38, N=4.04), Liquid crystal—isotropic phase transition temperature: 141° C., Crystal—liquid crystal transition temperature 121° C.

Example 21: Example of liquid crystalline composition

Mixed were 9 parts by weight of hydroquinone-bis (maleimidodecylcarbonyloxybenzoate) synthesized in Example 2 and 91 parts by weight of piperazine-bisaspartimide of hydroquinone-bis (maledimidopentylcarbonyloxybenzoate) synthesized in Example 5, followed by dissolution on a hot plate while heating to 150° C. As a result of observation of the resulting composition under a polarizing microscope equipped with a hot stage while slowly cooling, the resulting composition gradually came to have a liquid crystalline phase at 135 to 140° C. and the liquid crystalline phase was observed even at room temperature (25° C.).

Example 22: Example of liquid crystalline composition
Mixed were 30 parts by weight of hydroquinone-bis (malemidopentylcarbonyloxybenzoate) synthesized in Example 5 and 70 parts by weight of piperazine-bisaspartimide of hydroquinone-bis (maledimidodecylcarbonyloxybenzoate) synthesized in Example 10, followed by dissolution on a hot plate while heating to 150° C. As a result of observation of the resulting composition under a polarizing microscope equipped with a hot stage while slowly cooling, the resulting composition gradually came to have a liquid crystalline phase at 130 to 120° C. and the liquid crystalline phase was observed even at room temperature (25° C.).

Example 23: Example of liquid crystalline composition
Mixed were 90 parts by weight of hydroquinone-bis (malemidopentylcarbonyloxybenzoate) synthesized in Example 1 and 10 parts by weight of hydroquinone-bis (malemidopentylcarbonyloxybenzoate) synthesized in Example 2, followed by dissolution on a hot plate while heating to 150° C. As a result of observation of the resulting composition under a polarizing microscope equipped with a hot stage while slowly cooling, the resulting composition gradually came to have a liquid crystalline phase at 130 to 140° C. and the liquid crystalline phase was observed even at room temperature (25° C.).

Example 24: Example of liquid crystalline composition
Mixed were 10 parts by weight of hydroquinone-bis (malemidopentylcarbonyloxybenzoate) synthesized in Example 2, 85 parts by weight of piperazine-bisaspartimide of hydroquinone-bis(malemidopentylcarbonyloxybenzoate) synthesized in Example 5 and 5 parts by weight of a fluorine-substituted phenyltolan derivative synthesized in Example 20, followed by dissolution on a hot plate while heating to 150° C. As a result of observation of the resulting composition under a polarizing microscope equipped with a hot stage while slowly cooling, the resulting composition gradually came to have a liquid crystalline phase at 130 to 140° C. and the liquid crystalline phase was observed even at room temperature (25° C.).

[Advantages of the Invention]
The present invention can provide novel liquid crystalline bismaleimide containing a cross-linkable mesogenic group and oligomeric liquid crystalline bismaleimide; a liquid crystalline medium for electro-optical display, which comprises said liquid crystalline bismaleimide and/or said oligomeric liquid crystalline bismaleimide; and production processes thereof.

What is claimed is:
1. A bismaleimide comprising a mesogenic group, characterised in that it consists, corresponding to (I), of two reactive terminal maleimide groups which are linked via linear or singly alkyl-substituted alkylene chains A, which are linked to an aromatic mesogen M via ester, amide or ether groups,

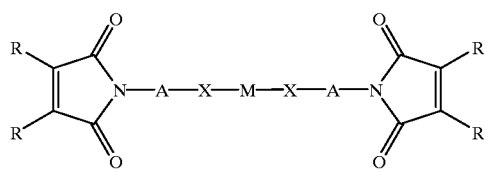

(I)

wherein A independently represents an alkylene chain comprising 3 to 20 $CH_2$ groups, wherein one C atom of each alkylene chain A may be chiral due to alkyl substitution, X independently represents —C(O)O—, —C(O)NH— or —O—, and M represents a mesogen consisting of at least two rings, which are linked para to each other by single bond, —$CH_2$—$CH_2$—, —CH=CH—, —C≡C—, —COO—, —CONH—, —C($CH_3$=CH—, —CH=N—, —CH=N—N=CH—, —N=N— or —N(O)=N— groups, and which may be mono- or di-substituted by alkyl groups, wherein the terminal aromatic rings are each substituted in the para position to these linking groups by an O or NH group of X, and R independently represents an H atom, an alkyl group comprising 1 to 8 C atoms, a phenyl ring or a halogen atom.

2. An oligomeric liquid crystalline bismaleimide of general formula (II)

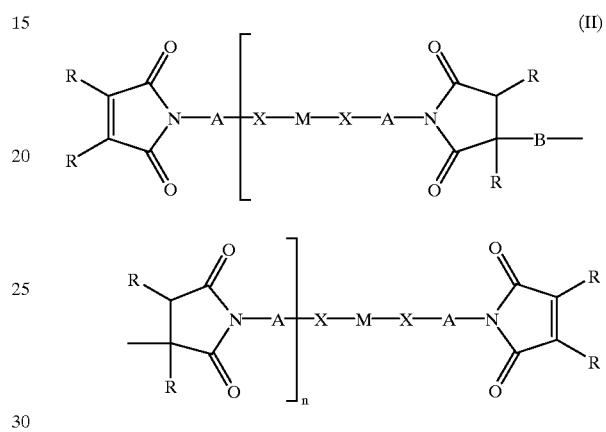

(II)

wherein A, X, M and R are defined as in claim 1, n represents an integer from 1 to 100 and B represents piperazinyl or a divalent radical which is derived from a primary or secondary parasubstituted cyclic diamine, wherein B is bonded via the amino groups of the diamine.

3. An oligomeric liquid crystalline bismaleimide according to claim 2, characterised in that B represents piperazinyl.

4. An oligomeric liquid crystalline bismaleimide according to claim 2, characterised in that B represents the divalent radical of a para-substituted aromatic primary or secondary diamine.

5. A method of producing bismaleimides comprising mesogenic groups of general formula (I) as defined in claim 1, in which X represents —C(O)O— or —C(O)NH—, characterised in that maleimidoalkylcarboxylic acids of general formula

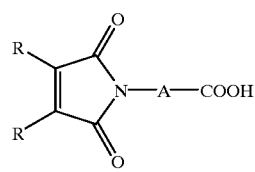

wherein R and A are as defined in claim 1, are converted into the corresponding acid chloride, 2 equivalents of the acid chloride are reacted with a compound of formula

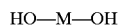
HO—M—OH or

$H_2$—N—M—$NH_2$, wherein M is defined as in claim 1, in a suitable solvent, optionally in the presence of a catalyst and/or an acid acceptor, and at a temperature of 0 to 70° C., and the bismaleimide is isolated.

6. A method of producing bismaleimides comprising mesogenic groups of general formula (I) as defined in claim 1, wherein X represents —O—, characterised in that
(i) a compound of general formula HO—M—OH, wherein M is defined as in claim 1, is reacted with 2 equivalents of an αω-haloalkane nitrile of general formula

wherein Hal represents a halogen atom and A' represents an alkylene chain comprising 2 to 19 CH$_2$ groups, and wherein one C atom of each alkylene chain A' can be chiral due to alkyl substitution, in a suitable aprotic dipolar solvent, in the presence of a catalyst and/or of an acid acceptor, and at a temperature of 20 to 200° C. to form an α, ω-dinitrile of general formula

wherein A' and M are as defined as above,
(ii) the α, ω-dinitrile is reduced with a complex metal hydride in the presence of a strong acid with subsequent hydrolysis to form the corresponding α, ω-diamine of general formula

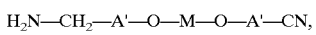

wherein A' and M are defined as above,
(ii) the α, ω-dinitrile is reduced with a complex metal hydride in the presence of a strong acid with subsequent hydrolysis to form the corresponding α, ω-diamine of general formula

wherein A' and M are defined as above, and
(iii) the α, ω-diamine is imidised with two equivalents of a maleic anhydride of general formula

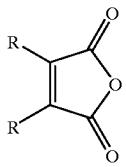

wherein R is as defined in claim 1, in a mixture consisting of an aliphatic carboxylic acid and an aromatic hydrocarbon at a temperature of 100 to 180° C., with the separation of water, to form the bismaleimides.

7. A method of producing bismaleimides comprising mesogenic groups of general formula (1) as defined in claim 1, wherein X represents —O—, characterised in that 2 equivalents of a halogenated N-alkylmaleimide of general formula

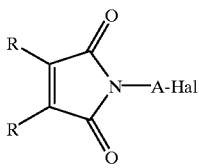

wherein R and A are defined in claim 1 and Hal represents a halogen atom, are reacted with a compound of general formula

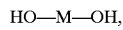

wherein M is defined as claim 1, in a suitable solvent, in the presence of a catalyst or an acid acceptor, and at a temperature of 20 to 200° C. and the bismaleimide is isolated.

8. A method of producing bismaleimides comprising mesogenic groups of general formula (I) as defined in claim 1, wherein X represents —O—, characterised in that maleic anhydride is reacted with a diamine of general formula H$_2$—N—A—X—M—X—A—NH$_2$, wherein A, M and X are as defined in claim 1, in dimethylformamide in the presence of acetic anhydride and of a catalyst consisting of nickel(II) acetate and triethylamine, at a temperature of 90 to 105° C.

9. A method of producing oligomeric bismaleimides comprising mesogenic groups corresponding to general formula (II) as defined in claim 2, characterised in that bismaleimides comprising mesogenic groups of general formula (I)

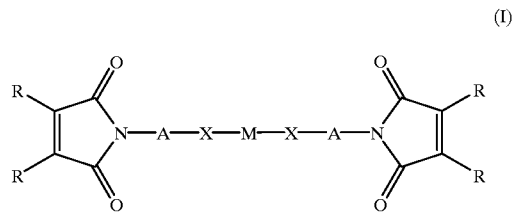

wherein A independently represents an alkylene chain comprising 3 to 20 CH$_2$ groups, wherein one C atom of each alkylene chain A may be chiral due to alkyl substitution, X independently represents —C(O)O—, —C(O)NH— or —O—, and M represents a mesogen consisting of at least two rings, which are linked para to each other by single bond, —CH$_2$—CH$_2$— CH=CH—, C=C—, —COO—, COHN—, —C(CH$_3$=CH—, CH=N—, CH=N—N=CH—, N=N—or —N(O)=N— groups, and which may be mono- or di-substituted by alkyl groups, wherein the terminal aromatic rings are each substituted in the para position to these linking groups by an O or NH group of X, and R independently represents an H atom, an alkyl group comprising 1 to 8 C atoms, a phenyl ring or a halogen atom, are oligomerised by a Michael addition, in a suitable solvent, with half to one equivalent of a para-substituted aromatic, alicyclic or heterocyclic primary or secondary diamine, at a temperature of 0 to 80° C., and the reaction product is isolated by methods known in the art.

10. A liquid crystalline medium for electro-optical displays, wherein at least one component is a bismaleimide or an oligomeric liquid crystalline bismaleimide as defined in any one of claims 1 to 4.

11. A bismaleimide according to claim 1, wherein the rings of said mesogen M are selected from an aromatic ring and a heterocyclic ring.

12. A method according to claim 6, wherein said temperature in step (i) is 50 to 150° C.

13. A method according to claim 7, wherein said temperature is 50 to 150° C.

* * * * *